United States Patent [19]

Johnson

[11] Patent Number: 4,522,592
[45] Date of Patent: Jun. 11, 1985

[54] VALVE STRUCTURE FOR AN ORAL EVACUATOR SYSTEM

[76] Inventor: W. Grant Johnson, 1642 Mockingbird Pl., Orange, Calif. 92667

[21] Appl. No.: 518,925

[22] Filed: Aug. 1, 1983

[51] Int. Cl.³ .............................................. A61C 17/04
[52] U.S. Cl. ..................................... 433/95; 251/340; 251/348; 604/902
[58] Field of Search ............................ 433/95, 93, 91; 251/337, 348, 347, 340, 321; 604/118, 119, 902, 33

[56] References Cited

U.S. PATENT DOCUMENTS

| | | | |
|---|---|---|---|
| 2,369,356 | 2/1945 | Koehn | 251/340 |
| 3,232,578 | 2/1966 | Cousins | 604/119 |
| 4,015,336 | 4/1977 | Johnson | 433/95 |
| 4,081,176 | 3/1978 | Johnson | 433/95 |
| 4,430,073 | 2/1984 | Bemis et al. | 604/902 |

*Primary Examiner*—John J. Wilson
*Attorney, Agent, or Firm*—Jackson, Jones & Price

[57] ABSTRACT

A hand-held valve structure for use with an oral evacuator system of the type which includes a vacuum source/waste disposal unit connected to the valve structure through a flexible vacuum hose. The valve structure includes an elongated body member having a central bore which is coupled to the vacuum hose. The upstream end of the body member includes a valve seat which surrounds the central bore. A poppet or valve piece, which is positioned adjacent the valve seat, is secured to the one end of a connecting rod, the rod being slidably-mounted on the body member. A detachable cover having a central bore is secured over the valve seat of the body member. The cover is provided with a slot which provides access to the connecting rod. A thumb latch is provided which is connected to the connecting rod through the cover member slot. A cam spring is positioned around the body member and engages the thumb latch so as to latch the poppet in either an open or a closed position. The slot or access opening is positioned downstream of the valve so that any entrapped flowable material upstream of the valve is prevented from escaping through the access opening or slot when the valve is closed.

11 Claims, 5 Drawing Figures

U.S. Patent   Jun. 11, 1985   4,522,592
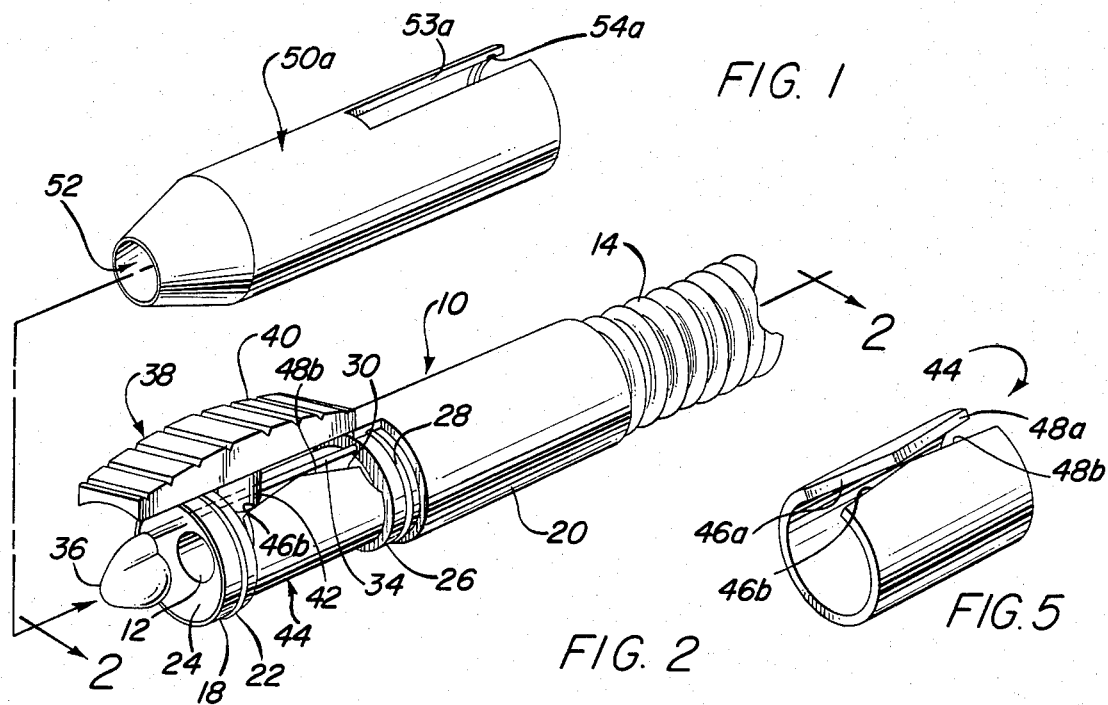
FIG. 1
FIG. 2
FIG. 5
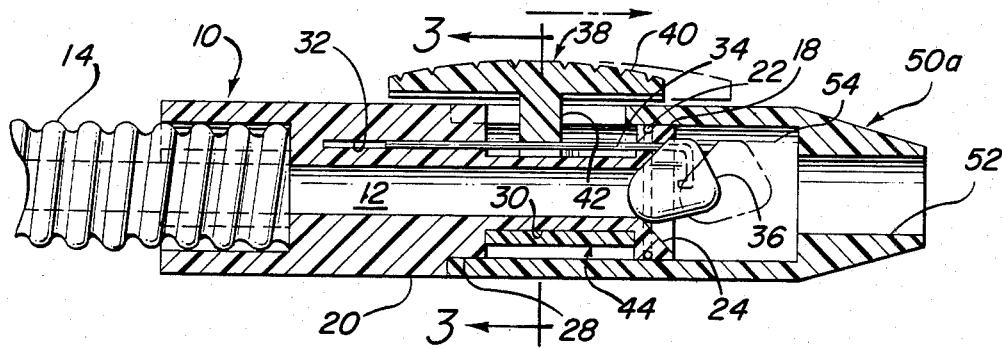
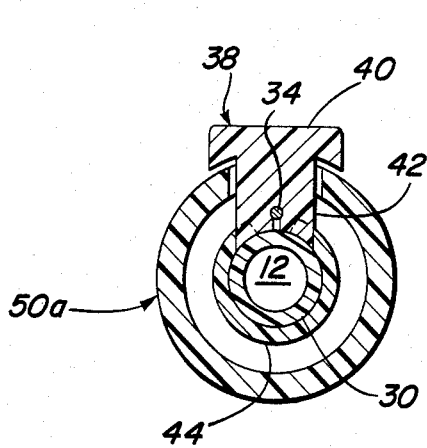
FIG. 3
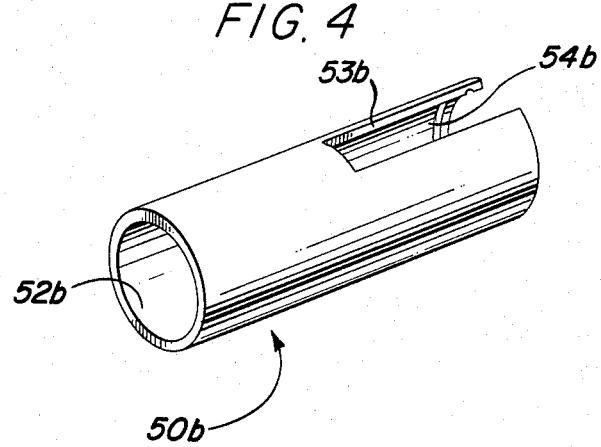
FIG. 4

VALVE STRUCTURE FOR AN ORAL EVACUATOR SYSTEM

BACKGROUND OF THE INVENTION

1. Field of the Invention

The present invention relates generally to valve structures and more particularly to valve structures located in the hand-held portion of an oral evacuator system used in dental procedures.

2. Background Art

Oral evacuator systems are used in dental procedures to facilitate the removal of fluids and debris from the mouth of dental patients. Such evacuator systems include a hand-held portion which is connected to a vacuum source/waste disposal unit by way of a flexible hose. The hand-held portion includes a valve structure which may be actuated by either the patient or the dentist.

U.S. Pat. No. 4,015,336 issued to the present applicant discloses an exemplary prior art valve structure for use in an oral evacuator system. The valve structure includes an elongated housing having an external manually-actuated latch for opening and closing the valve. A slot is provided in the side of the housing to permit passage of a connecting element between the latch and a spring-biased poppet disposed within the housing.

One of the primary disadvantages of such prior art valve structures is that fluid and debris tend to escape through the access slot in the housing when the valve is closed. Such leakage is largely attributable to the fact that the access slot is positioned upstream of the valve. Thus, when the valve is closed, matter entrapped upstream of the valve can escape through the slot. Such prior art valve structures are also somewhat difficult to actuate, especially by persons having arithritic conditions and the like.

U.S. Pat. No. 4,081,176, also to applicant, discloses a valve structure which overcomes some of the disadvantages of the previously-described device. This structure avoids the use of openings in the housing with activation of the normally-closed valve being accomplished by manually extending a resilient element. However, in order to maintain the valve in an open position, it is necessary to maintain a constant force on the resilient element which can be quite tiring.

The present invention overcomes the above-noted disadvantages of the prior art. The valve structure disclosed herein has no tendency to leak and the valve may be easily activated and maintained in an open or closed position. These and other advantages of the present invention will become apparent to those skilled in the art upon reading the following detailed description of the invention together with the drawings.

SUMMARY OF THE INVENTION

A valve structure for use in an oral evacuator system of the type having a vacuum source/waste disposal device is disclosed. The structure includes a body unit having a central passageway which extends therethrough. One end of the unit includes apparatus for coupling the valve structure to a flexible hose which is connected to the vacuum source/waste disposal unit.

The valve structure further includes a valve for controlling flow through the central passageway. The valve is actuated between an open and closed position by an actuator which extends through an access opening located downstream from the valve. Thus, when the valve is closed, the flowable material which typically collects in the valve structure upstream of the valve is prevented from escaping through the access opening.

The body unit is preferably constructed in two pieces, including a body member and a detachable cover member which is secured over the upstream end of the body member. The body member is provided with a central bore which forms part of the central passageway. A valve seat is located at the upstream end of the body member which surrounds the bore. The cover member is also provided with a bore which is in communication with the bore of the body member. The cover member extends over the valve seat of the body member and includes the access opening which is in the form of a slot.

The valve is a poppet which engages the valve seat so as to close the passageway. The poppet is secured to one end of a connecting rod which is slidably mounted on the body member. A latch member is provided for manually actuating the poppet. The latch member includes an outer thumb contact element which is positioned outside the cover member. A connecting member which extends through the access opening is provided for connecting the thumb contact portion of the connecting rod. Thus, the valve may be opened and closed by manually manipulating the thumb contact element. A cam spring which engages the latch member may be further provided for latching the valve in either an open or a closed position.

BRIEF DESCRIPTION OF THE DRAWINGS

FIG. 1 is a perspective view of the subject valve structure with one of the interchangeable cover attachments removed.

FIG. 2 is a cross-sectional side view of the subject valve structure taken through section line 2—2 of FIG. 1.

FIG. 3 is a cross-sectional front view of the subject valve structure taken through section line 3—3 of FIG. 2.

FIG. 4 is a perspective view of another interchangeable cover attachment for the subject valve structure.

FIG. 5 is a perspective view of a cam spring used in the subject valve structure.

DETAILED DESCRIPTION OF THE INVENTION

Referring now to the drawings, a preferred embodiment of the subject valve structure may be seen. Unless otherwise indicated, all elements of the valve structure are preferably fabricated from high impact plastic. The structure includes a tubular body member, generally designated by the numeral 10. As can best be seen in FIGS. 2 and 3, the body member is provided with an axial bore 12 which extends entirely through the member.

One end of body member 10 is provided with an annular opening (not designated) which is coaxial with bore 12. The annular opening is adapted to receive one end of flexible vacuum hose 14. The end of the hose is friction fitted within the annular opening to form a generally airtight seal. The remaining end of vacuum hose 14 is to be connected to a vacuum source (not shown).

The other end of body member 10, the upstream end, is provided with a valve seat element 18 having a diameter which is somewhat less than the diameter of the central portion 20 of the member. The valve seat element includes a circular recess (not designated) for securing an O-ring 22. The upstream end of element 18 is beveled to form a valve seat 24.

A C-shaped recess is formed in the body member 10 adjacent central portion 20 which defines a reduced diameter body section 26. Body section 26, which has a diameter equal to or greater than that of valve seat element 18, is provided with a circular ridge 28. As will be subsequently described, ridge 28 is used to secure interchangeable cover attachments.

A section 30 of body member 10 is disposed between valve seat element 18 and body section 26. Section 30 has a diameter somewhat smaller than that of section 26 and valve seat element 18.

A small diameter guide opening 32 (FIG. 2), which is parallel to central bore 12, extends completely through valve seat element 18 of body member 10 and partially through central portion 20 of the body member. Openings 32 receive a connecting rod 34 which is preferably fabricated from heavy-gauge wire. Connecting rod 34 is slidably mounted within opening 32 and includes a bent end section which is used to secure a valve member or poppet 36 to the rod.

Valve member 36 is formed from a resilient material such as rubber using conventional injection molding techniques. The member is molded over the bent end section of rod 34 thereby securing the rod and member together. Member 36 is provided with a rounded surface (not designated) which conforms generally to the surface of valve seat 24. The rounded surface extends around rod 34 so that opening 32 in which the rod 34 is mounted is sealed when the valve is closed.

The valve structure is operated by a manually operable latch member, generally designated by the numeral 38. Latch member 38 includes a serrated thumb contact portion 40 and a connecting member 42. Connecting member 42 has a generally circular cross-section and is transverse to the longitudinal axis of body member 10. As can best be seen in FIG. 3, connecting member 42 has a notch (not designated) into which rod 34 is press-fitted. Member 42 may be further rigidly secured to rod 34 by adhesives or any other suitable manner. The bottom surface of connecting member 42 is rounded and conforms to the outer diameter of section 30 of body member 10 so that the member will slide smoothly across the surface of the section 30.

The valve structure further includes a cam spring 44 which is preferably manufactured from a springy plastic material. As can best be seen in FIG. 5, cam spring 44 is generally in the form of a cylinder having a longitudinal section removed therefrom. The removed section is in the form of an hourglass so that two pairs of opposing surfaces 46a, 46b and 48a, 48b are formed. These surfaces are preferably at an acute angle with respect to the longitudinal axis of the spring.

Cam spring 44 is disposed over section 30 of body member 10 with the connecting member 42 of the latch member being positioned either between opposing surfaces 46a, 46b or 48a, 48b. The spring is positioned around section 30 by forcing the opposing faces apart until the hourglass gap is sufficiently wide to pass over the section and then releasing the spring. Longitudinal movement of spring 44 is limited by valve section element 18 and body section 26. Rotational movement of the spring 44 is restricted by connecting member 42.

The valve structure further includes one or more interchangeable cover attachments. One such cover attachment is shown in FIGS. 1 and 2 and is generally designated by the numeral 50a. Cover attachment 50a is generally cylindrical in shape and is provided with a central axial bore (not designated) which has a diameter slightly larger than the diameter of body section 26 and valve seat element 18 (FIG. 2). Attachment 50a further includes a reduced diameter bore 52 at the upstream portion of the attachment which is coaxial and in communication with the central bore. The upstream portion of cover attachment 50a tapers to a diameter slightly larger than bore 52.

Cover attachment 50b (FIG. 4) is provided with a narrow cutout or slot 53b in the sidewall of the attachment at the downstream end thereof for accommodating connecting member 42 of the latch member 38. The inner surface of attachment 50b at the downstream end includes a circular recess (FIG. 1) adapted to receive circular ridge 28 of the body member. As shown in FIG. 2, when cover attachment 50a is fitted over the upstream end of the body member, a chamber 54 is formed upstream of valve member or poppet 36. O-ring 22 serves to effectuate a seal between valve seat element 18 and the inner wall of cover attachment 50a. Slot 53a receives the projection (not designated) which is formed adjacent body section 26 and which extends from central portion 20. The projection ensures correct alignment of cover attachment 50a on the body member and prevents the cover attachment from rotating so as to interfere with movement of latch member 38. In addition, the projection serves as a guide for the latch member 38 and, together with cover attachment 50a, maintains thumb contact portion 40 parallel with connecting rod 34 and opening 32.

Having disclosed the details of the construction of the subject valve structure, the operation of the device will now be described. Cover attachment 50a is adapted for use with a conventional surgical suction tip. The tip is in the form of an elongated tube having an outer diameter which is slightly smaller than bore 52 of cover attachment 52a. The tip is installed by inserting the mounting end into opening 52 and is retained therein by friction. The free end (not shown) of vacuum hose 14 is coupled to a conventional oral evacuator vacuum source/waste disposal unit.

When the thumb portion of latch member 38 is moved by the patient or dentist towards the upstream position, poppet or valve member 36 is forced out of engagement with valve seat 24 as shown in FIG. 1. Thus, the valve is in an open position so that airflow will occur through the surgical suction tip, chamber 54, body member 10 and down to the vacuum source through vacuum hose 14. Fluids, debris and other flowable material near the input of the wand will be entrapped in the airflow and transported to the vacuum source/waste disposal unit.

When valve member 36 is in the open position, opposing shoulders 46a and 46b of cam spring 44 exert a force on connecting member 42 which urges the valve member to remain open. Thus, the valve will remain latched in the open position without the necessity of applying further force to latch member 38.

The valve structure is switched to a closed position by manually shifting latch member 38 to a downstream position as shown in FIG. 2 with connecting member 42 being positioned between opposing shoulders 48a and 48b of cam spring 44. In this position valve member 36 becomes seated in valve seat 24, thereby effectuating a seal. Cam spring 44 and connecting member 42 are dimensioned such that the spring will exert a constant force on the connecting member so that valve element 36 will be urged into contact with valve seat 24. Thus, the valve will remain secured in the closed position without the necessity of applying further force to latch member 38. Thus, airflow and the transfer of flowable matter to the vacuum source/waste disposal unit is terminated.

A metal spring may be substituted for plastic cam spring 44, although the plastic spring is preferred. The metal spring is fabricated from spring wire and is bent to form a generally hourglass shape. The spring is positioned over section 30 of the body member and extends around connecting member 42. The lower section of the spring is positioned adjacent body section 26 with the upper section of the spring being positioned adjacent valve seat element 18. The upper side elements of the spring form opposing resilient surfaces which correspond to surfaces 46a and 46b of cam spring 44 with the lower side elements forming surfaces which correspond to surfaces 48a and 48b.

When the valve is closed, it is possible that flowable matter will collect in chamber 54. However, inasmuch as the access opening for coupling the thumb contact member 40 to connecting rod 34 is downstream of valve 36, the material is prevented from escaping through the access opening. Note that member 36 also extends over opening 32 thereby preventing leakage around rod 34.

FIG. 4 illustrates a second cover attachment, generally designated by the numeral 50b. Attachment 50b is adapted to receive a funnel (not shown). Attachment 50b is generally cylindrical in shape with a central bore 52b having a diameter slightly larger than that of valve seat element 18 and section 26 of body member 10. The attachment further includes an elongated cutout or slot 53b in the sidewall and a recess 54b similar to the corresponding elements 53a and 54a of attachment 50a. Attachment 50b functions in the same manner as the previously-described attachment with the funnel base being inserted in bore 50b at the upstream end of the unit.

Thus, a novel valve structure for an oral evacuator has been disclosed. While one embodiment of the structure has been described in some detail, it is to be understood that certain changes obvious to those skilled in the art can be made without departing from the spirit and scope of the invention as defined by the appended claims.

What is claimed is:

1. In an oral evacuator system, a valve structure to be coupled to a vacuum source/waste disposal device of the system by way of a flexible conduit, said valve structure comprising:
   an elongated body unit having a central passageway extending therethrough, said body unit having an upstream end with a valve seat around said passageway, a downstream end and a centrally-located mechanism area essentially isolated from said upstream end;
   coupling means at said downstream end of said body unit for coupling said central passageway to the flexible conduit;
   valve means disposed adjacent said valve face for opening and closing said central passageway;
   actuating means isolated from the upstream end, including means slidably and sealably seated in a valve actuating passageway located between the central and upstream portions, said slidable means connected to said valve means for actuating said valve means; and
   said actuating means further comprising means for positively placing said valve means in either an open or a closed position.

2. The valve structure of claim 1 wherein said elongated body unit includes a detachable cover member which extends over said valve seat and which may be removed free of leakage while said valve means is closed.

3. The valve structure of claim 2 wherein the outer surface of said upstream and central portions are defined by said cover member.

4. The valve structure of claim 3 wherein said valve means includes a poppet which engages said valve seat.

5. The valve structure of claim 4 wherein said actuating means includes a connecting rod generally parallel to said central passageway and slidably mounted on said body member, said connecting rod having an end connected to said poppet.

6. The valve structure of claim 5 wherein said actuating means further includes a latch member comprising a thumb contact member disposed outside said body unit and a connecting member attached to said thumb contact member which extends through an access opening in the central portion to engage said connecting rod.

7. The valve structure of claim 6 wherein said actuating means further includes biasing means for urging said poppet into engagement with said valve seat when said valve means is in said open position and for urging said poppet out of engagement with said valve seat when said valve means is in said closed position.

8. The valve structure of claim 7 wherein said biasing means includes a cam spring which extends around said body member at said central portion and which engages said connecting member of said latch member.

9. In an oral evacuator system, a valve structure to be coupled to a vacuum source/waste disposal device of the system by way of a flexible conduit, said valve structure comprising:
   an elongated body member having a central passageway extending therethrough and a valve seat extending around said central passageway, said body member having an upstream end, a downstream end and a centrally-located access opening;
   coupling means at said downstream end of said body member for coupling said central passageway to the flexible conduit;
   a cover member which extends over said upstream end and said valve seat of said body member, said cover member having a central bore which is in communication with said passageway and an isolated access opening in a sidewall of said cover member which is disposed around said centrally-located access opening;
   valve means disposed at said valve seat for opening and closing said passageway, said valve means includes a poppet and a slidably-mounted connecting rod having an end thereof connected to said poppet and an operating end thereof located in said access opening; and actuating means which extends through said access opening for actuating said valve means between an open and a closed position.

10. The valve structure of claim 9 wherein said actuating means further includes a cam spring extending around said body member which engages said latch member.

11. In an oral evacuator system, a valve structure to be coupled to a vacuum source/waste disposal device of the system by way of a flexible conduit, said valve structure comprising:
- an elongated body member having a central passageway extending therethrough and a valve seat extending around said central passageway, said body member having an upstream end and a downstream end;
- coupling means at said downstream end of said body member for coupling said central passageway to the flexible conduit;
- a cover member which extends over said upstream end and said valve seat of said body member, said cover member having a central bore which is in communication with said passageway and an access opening in a sidewall of said cover member which is disposed downstream from said valve seat;
- valve means disposed at said valve seat for opening and closing said passageway, said valve means includes a poppet;
- actuating means which extend through said access opening for actuating said valve means between an open and a closed position, including a slidably-mounted connecting rod having an end thereof connected to said poppet, a latch member having a thumb contact member disposed outside said cover member, and a connecting member attached to said thumb contact member which extends through said access opening and engages said connecting rod; and
- said actuating means further includes a cam spring extending around said body member which engages said latch member.

* * * * *